United States Patent [19]

Anderson et al.

[11] Plant 4,994

[45] Mar. 15, 1983

[54] PISTACHIO TREE

[76] Inventors: Henry P. Anderson; Kenneth L. Puryear, both c/o Pioneer Nursery, 800 N. Chester, Bakersfield, Calif. 93308

[21] Appl. No.: 286,884

[22] Filed: Jul. 27, 1981

[51] Int. Cl.[3] ..... A01H 5/03

[52] U.S. Cl. ..... Plt./30

[58] Field of Search ..... Plt./30

*Primary Examiner*—Robert E. Bagwill

[57] ABSTRACT

This invention relates to a new and different variety of pistachio tree primarily identified by its rounded spreading growth habit, pleasing green color of mature foliage and its production of male flowers and pollen.

3 Drawing Figures

The present invention relates to a new and distinct variety of pistachio tree, the variety being primarily characterized, as to novelty, by vigorous rounded growth habit and the abundant production of male (staminate) flowers and pollen.

The variety is further characterized by abundant foliage of pleasing medium green color and the production of pollen necessary to fertilize a female (seed bearing) pistachio tree.

A tree which is vigorous, of rounded shape with semi-glossy to matte foliage with pointed leaflets; the flowers being borne in drooping clusters (catkins) or bunches similar to grapes (see photo). The tree, which has a normal height of 15 to 20 feet when mature and a spread usually wider than tall (see photo).

A plant which grows and flowers satisfactorily in any well drained soil and produces sufficient pollen to fertilize another selected female pistachio variety for seed (propagation) purposes.

Variety Name: Identification number — PN-46-M.

The present variety of pistachio was originated and selected by us at our orchards located at Delano, Kern County, Calif., under conditions of careful control and observation, as a selection from numerous seedlings of several species and hybrids being grown and tested at the time in our search for improved pistachio understocks on which to bud of graft commercial nut bearing varieties.

Subsequent to origination of the variety we successfully asexually reproduced it at our orchard/nursery, located as aforesaid, by budding and by grafting, the reproductions having run true in all respects.

The color photographs illustrate the variety, including mature tree, foliage and flower clusters. (Photo of flower clusters made on Mar. 14, 1981).

Referring now specifically to the new and distinct variety of pistachio tree, the following is a detailed description thereof in outline; all major color plate identifications, if any, being by reference to the British Colour Council Horticultural Colour Chart, except where common terms of color definition are employed.

Flowers borne in clusters of many individual male flowers, similar to a bunch of grapes (see photo).

Quantity of bloom: Abundant.

Buds: Very small in size and of brownish color.

Bloom:

*Size when fully open.*—Very small, with blooms opening at random over period of several days (15–18) to cover an extended period of pollination. Referring to photo of bloom clusters: (1) Flowers (male) first started to open on Feb. 23, 1981; (2) Feb. 28, 1981 — male (present variety) was in peak bloom; (3) On Saturday, Mar. 14, 1981 (date photo was taken) bloom was 99% over.

Color:

*Flower cluster.*—From tree in seed orchard, Delano, Calif. — Stems of bunches are medium green, often tinted or shaded brownish; flowers — greenish to brownish.

Reproductive organs: All male:

*Stamens.*—Arranged regularly about center of flower.

*Filaments.*—Very short.

*Anthers.*—Well formed.

*Pollen.*—Abundant.

Foliage:

*Leaves.*—Compound of eight (sometimes more).

*Leaflets.*—Medium small, leather, semi-glossy to matte. Shape: long, narrow (lanceolate); apex acute; base acute but less so than apex. Color: medium green, new growth — normal (medium) green, near Spinach Green 0960, often tinted reddish, especially young leaves on tips of shoots. Ribs (center) of leaves and center rib of leaflets usually lighter color (yellowish green) than rest of leaf surface. Length of leaves (including petiole and leaflets) may average about eight inches (or more); to end of midrib, 5–7 inches. Individual leaflets may be 3 to 4 inches (sometimes more) in length.

*Growth.*—Habit — upright when young, becoming much branched and spreading (wider than tall) at maturity. Tree usually has several main branches (without central leader). These main branches support many lesser limbs and branches to form a dense symmetrical crown.

*Color.*—Main branches and limbs — gray to brownish.

The new variety of pistachio tree as herein described may vary in slight detail due to climatic, soil and cultural conditions under which the variety may be grown; the present description being of the variety as grown at Delano, Calif.

The following is claimed:

1. A new and distinct variety of pistachio tree, identified as PN-46-M, characterized by a mature tree of rounded, spreading shape, wider than tall, having several main branches without central leader; rapid growth, abundant, leathery, healthy foliage, ease of propagation by budding or grafting; and further characterized by the abundant production of male flowers, in clusters, which produce pollen especially desirable for pollenizing a selected variety of female pistachio tree identified as PN-17-F for the production of hybrid seeds, said hybrid seeds producing a fast growing, disease resistant tree of value for use as understock upon which to bud or graft commercial nut bearing varieties of pistachio such as 'Kerman'.

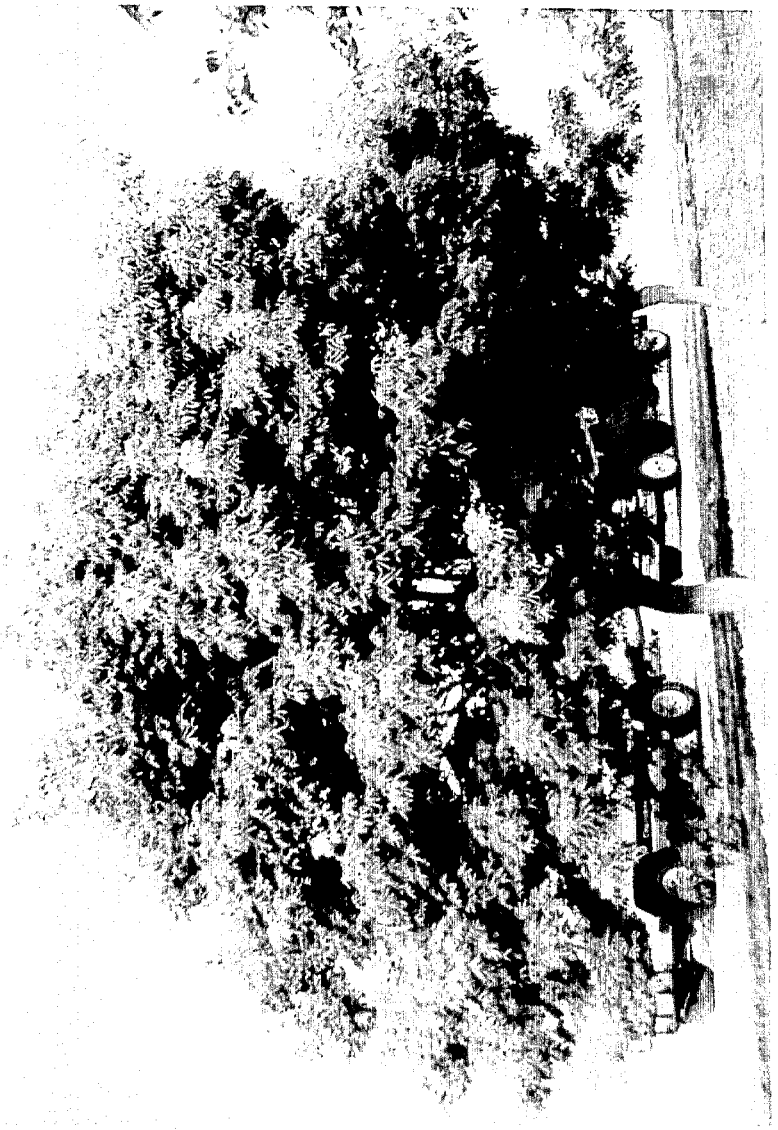

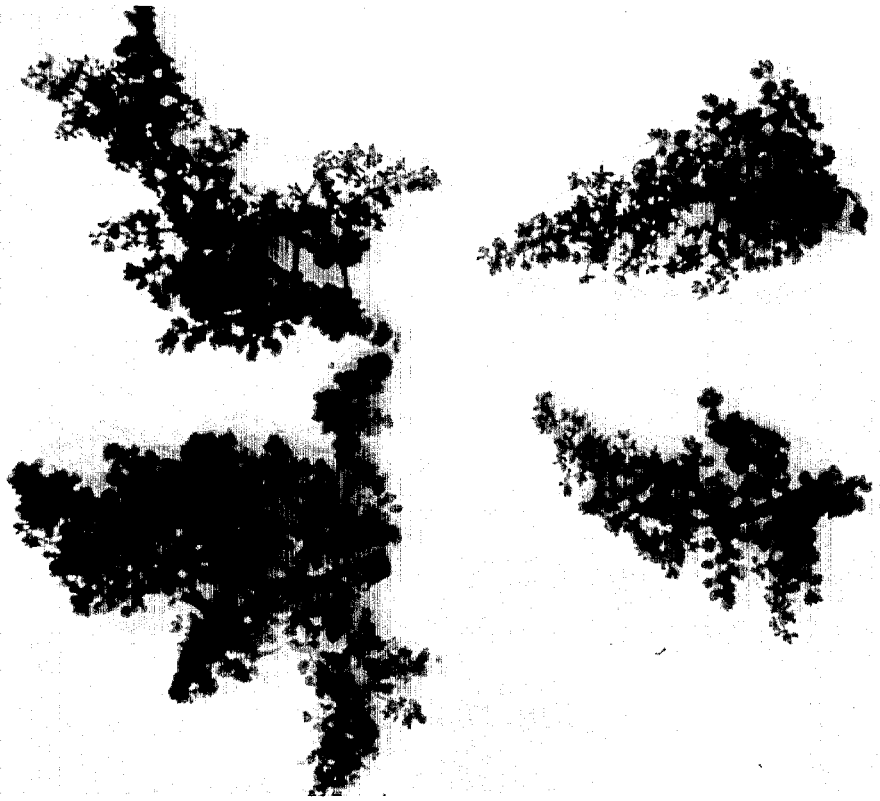
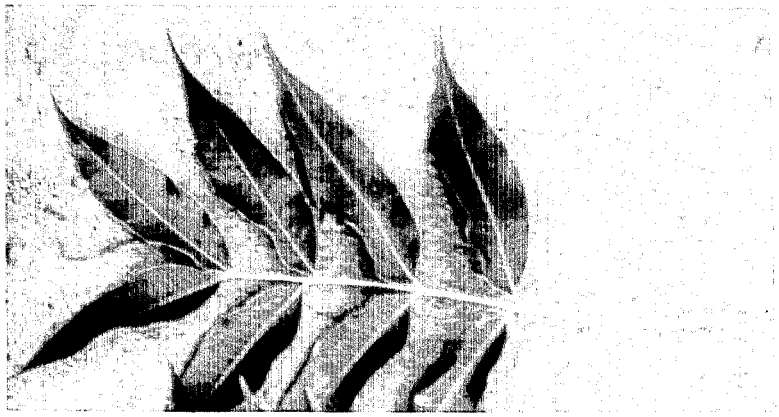

* * * * *